United States Patent
Barry, Jr. et al.

(10) Patent No.: US 9,861,736 B2
(45) Date of Patent: Jan. 9, 2018

(54) METHODS FOR EXTRACTING PLATELET-RICH PLASMA FOR THERAPEUTIC INJECTION

(71) Applicant: Fenwal, Inc., Lake Zurich, IL (US)

(72) Inventors: John W. Barry, Jr., Mount Prospect, IL (US); Brian C. Case, Lake Villa, IL (US); Jonathan Prendergast, Palatine, IL (US); Lan T. Nguyen, Vernon Hills, IL (US); John Foley, Wheeling, IL (US)

(73) Assignee: Fenwal, Inc., Lake Zurich, IL (US)

( * ) Notice: Subject to any disclaimer, the term of this patent is extended or adjusted under 35 U.S.C. 154(b) by 432 days.

(21) Appl. No.: 13/907,311

(22) Filed: May 31, 2013

(65) Prior Publication Data

US 2014/0357465 A1    Dec. 4, 2014

(51) Int. Cl.
| | |
|---|---|
| *A61M 1/36* | (2006.01) |
| *A61M 1/02* | (2006.01) |
| *A61M 1/34* | (2006.01) |

(52) U.S. Cl.
CPC ............ *A61M 1/3693* (2013.01); *A61M 1/02* (2013.01); *A61M 1/3496* (2013.01); *A61M 1/3696* (2014.02); *A61M 2202/0415* (2013.01)

(58) Field of Classification Search
CPC ..... A61M 1/02; A61M 1/3496; A61M 1/3693
USPC .............................................. 494/16, 37, 45
See application file for complete search history.

(56) References Cited

U.S. PATENT DOCUMENTS

| | | | |
|---|---|---|---|
| 5,370,802 A | 12/1994 | Brown | |
| 5,868,696 A | 2/1999 | Giesler et al. | |
| 6,322,488 B1 | 11/2001 | Westberg et al. | |
| 6,582,349 B1 | 6/2003 | Cantu et al. | |
| 6,709,413 B1 | 3/2004 | Chance et al. | |
| 2002/0115585 A1* | 8/2002 | Hei ........................ | A61K 35/16 514/1 |
| 2003/0232712 A1 | 12/2003 | Dolecek | |

(Continued)

FOREIGN PATENT DOCUMENTS

WO    WO 89/04709 A1    6/1989

OTHER PUBLICATIONS

Extended European Search Report for European Patent Appln. No. 13178022.3, dated Dec. 15, 2014.

(Continued)

*Primary Examiner* — Dirk Bass
(74) *Attorney, Agent, or Firm* — Cook Alex Ltd.

(57) ABSTRACT

Methods are provided for collecting platelet-rich plasma. A disposable flow circuit is mounted to a fluid processing device having a fluid separation chamber and an injection device. A fluid containing plasma and platelets is continuously conveyed from a fluid source into the fluid separation chamber and processed to produce platelet-rich plasma. At least a portion of the platelet-rich plasma is automatically conveyed from the fluid separation chamber into the injection device, which is directly connected to a pump device such that at least a portion of the platelet-rich plasma from the fluid separation chamber is automatically conveyed into the pump device prior to being conveyed into the injection device. The injection device with the platelet-rich plasma is then detached from the disposable flow circuit.

14 Claims, 6 Drawing Sheets

(56) References Cited

U.S. PATENT DOCUMENTS

| | | | | |
|---|---|---|---|---|
| 2005/0245835 A1* | 11/2005 | Butler | ................. | A61B 5/0836 600/532 |
| 2007/0225686 A1* | 9/2007 | Shippert | ............ | A61M 1/0001 604/542 |
| 2010/0099778 A1* | 4/2010 | Wright | ............... | B29C 44/3442 514/723 |
| 2013/0131546 A1* | 5/2013 | Azimpoor | ......... | A61B 10/0096 600/566 |

OTHER PUBLICATIONS

"Magellan Autologous Platelet Separator" brochure, Arteriocyte Medical Systems, Inc., circa 2008.

\* cited by examiner

FIG. 7

# METHODS FOR EXTRACTING PLATELET-RICH PLASMA FOR THERAPEUTIC INJECTION

FIELD OF THE DISCLOSURE

The disclosure relates to blood processing systems and methods. More particularly, the disclosure relates to systems and methods for isolating platelet-rich plasma from blood or a fluid containing blood plasma and platelets for therapeutic infusion.

DESCRIPTION OF RELATED ART

A wide variety of fluid processing systems are presently in practice and allow for a fluid to be fractionated or separated into its constituent parts. For example, various blood processing systems make it possible to collect particular blood constituents, rather than whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor or patient, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood may be separated into its constituents by employing any of a number of methods and systems. One common method of separating blood is centrifugation. In continuous processes, this requires that the whole blood be passed through a centrifuge after it is withdrawn from, and before it is returned to, the blood source. To avoid contamination and possible infection (if the blood source is a human donor or patient), the blood is preferably contained within a preassembled, sterile fluid flow circuit or system during the entire centrifugation process. Typical blood processing systems thus include a permanent, reusable module or assembly containing the durable hardware (centrifuge, drive system, pumps, valve actuators, programmable controller, and the like) that spins and controls the processing of the blood and blood components through a disposable, sealed, and sterile flow circuit that includes a centrifugation chamber and is mounted in cooperation on the hardware.

The hardware engages and spins the disposable centrifugation chamber during a blood separation step. As the flow circuit is spun by the centrifuge, the heavier (greater specific gravity) components of the whole blood in the flow circuit, such as red blood cells, move radially outwardly away from the center of rotation toward the outer or "high-G" wall of the centrifugation chamber. The lighter (lower specific gravity) components, such as plasma, migrate toward the inner or "low-G" wall of the centrifuge. Various ones of these components can be selectively removed from the whole blood by providing appropriately located channeling seals and outlet ports in the flow circuit.

One use of separated blood components is platelet-rich plasma therapy. In such a procedure, platelet-rich plasma is separated from blood using any suitable method and/or system. Thereafter, the platelet-rich plasma is injected or infused into a patient for pain relief and/or other therapeutic purposes, such as for help in recovering from joint-related injuries. Key benefits of platelet-rich plasma are the autologous derivation of growth factors and its minimal adverse-effect profile. At this time, the regenerative, inflammatory-modulating, and wound healing hastening abilities of platelet-rich plasma are primarily being applied to recalcitrant circumstances, but other therapeutic uses for platelet-rich plasma, such as its applicability in treating musculoskeletal and vascular pathologies, are also being explored.

The MAGELLAN® autologous platelet separator from Arteriocyte Medical Systems of Cleveland, Ohio, is an example of a known system for separating platelet-rich plasma from blood for subsequent injection or infusion. Systems of this type may have a number of potential disadvantages. For example, the separator is separate from the blood draw apparatus, such that blood must be drawn or collected from a blood source and then transferred to the separator, which creates an opportunity for the blood to become contaminated. Additionally, the separator is a batch-type system, meaning that it is capable of only a small platelet yield for each separation cycle (i.e., enough for only a single syringe). Furthermore, there is no provision for returning unused blood components (e.g., separated red blood cells) to the blood source, if the blood source is a human. Accordingly, there remains room for improvement of known platelet separators of this type.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method is provided for processing a fluid containing blood plasma and platelets. The method includes continuously adding a fluid containing blood plasma and platelets into a fluid separation chamber and using the fluid separation chamber to isolate platelet-rich plasma therein. At least a portion of the platelet-rich plasma is automatically transferred from the fluid separation chamber into an injection device.

In one aspect, a method is provided for collecting platelet-rich plasma. The method includes mounting a disposable flow circuit to a fluid processing device having a fluid separation chamber and an injection device. A fluid containing plasma and platelets is continuously conveyed from a fluid source into the fluid separation chamber and processed to produce platelet-rich plasma therein. At least a portion of the platelet-rich plasma is automatically conveyed from the fluid separation chamber into the injection device, which is directly connected to a pump device such that at least a portion of the platelet-rich plasma from the fluid separation chamber is automatically conveyed into the pump device prior to being conveyed into the injection device. The injection device with the platelet-rich plasma is then detached from the disposable flow circuit.

In another aspect, a method is provided for collecting platelet-rich plasma. The method includes mounting a disposable flow circuit to a fluid processing device having a fluid separation chamber, a pump device fluidly connected to the fluid separation chamber, and an injection device directly connected to the pump device. The fluid processing device is operated to process a fluid containing plasma and platelets so as to produce platelet-rich plasma in the fluid separation chamber while the injection device is directly connected to the pump device. The pump device is operated to convey the platelet-rich plasma out of the fluid separation chamber and into the injection device directly connected to the pump device.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
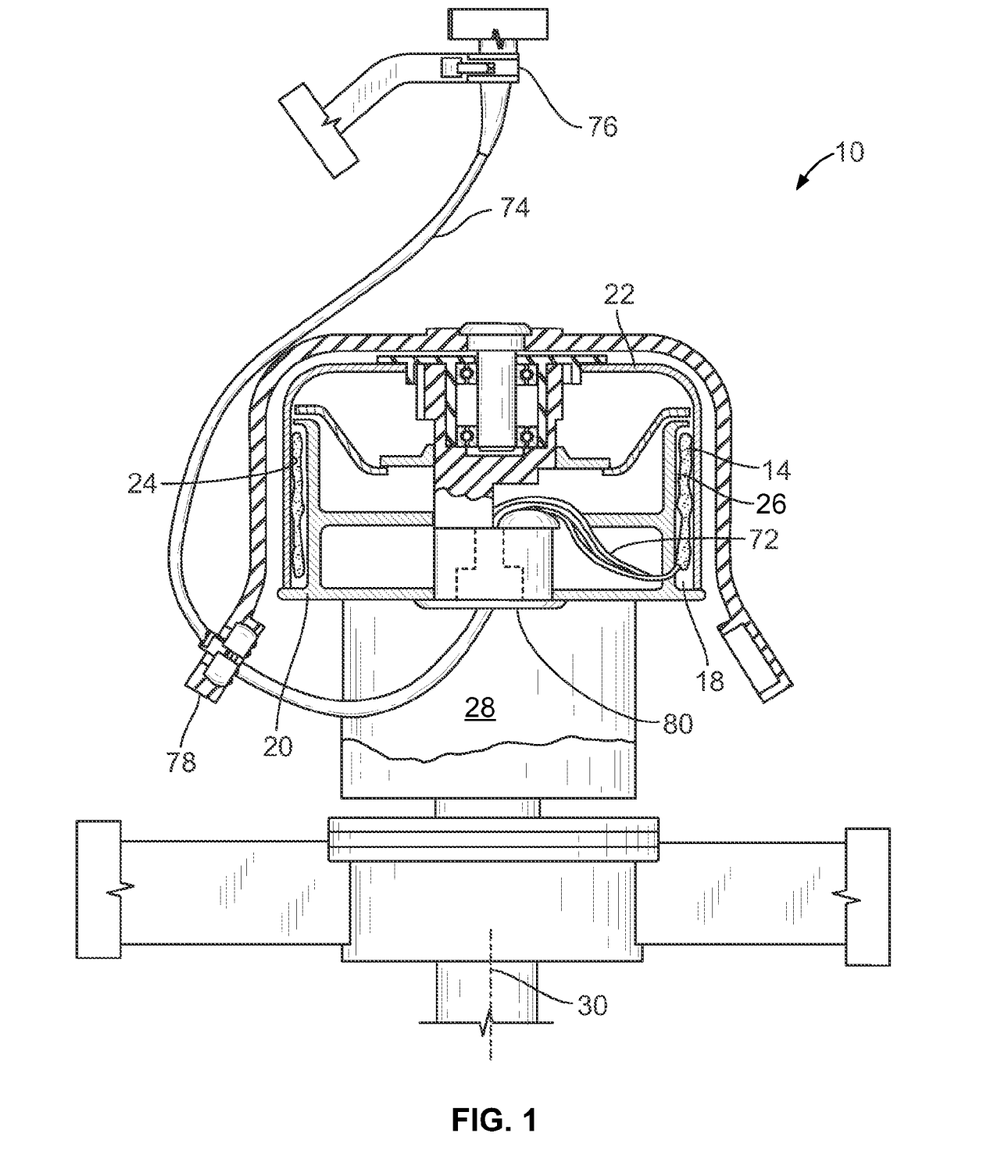
FIG. 1 is a side section view of a centrifuge receiving a fluid separation chamber of a disposable flow circuit.

FIG. 1 shows a centrifuge 10 of a fluid processing device 12 (FIG. 5) receiving a fluid separation chamber 14 of a disposable flow circuit 16 (FIG. 5), which is suitable for separating blood or any other fluid containing blood plasma and platelets. It should be understood that the present disclosure is not limited to the illustrated fluid processing device and disposable flow circuit, but may be applied to any other suitable combination of fluid processing device and flow circuit that can separate platelets from blood or a platelet-containing fluid. This may include different fluid processing devices including a centrifuge, as well as fluid processing devices that separate blood or fluid by means other than a centrifuge (e.g., a gradient disk). As for the blood or fluid to be separated, it may come from any suitable blood source. For example, the fluid source may be a living human or non-human animal whose bodily fluid is directly drawn into the device for processing. In other embodiments, the fluid to be processed does not come directly from a living human or non-human animal, but is instead provided directly from a non-living source, such as a container holding an amount of fresh or stored fluid (e.g., blood or a blood component that has been previously drawn from a living source and stored). In additional embodiments, there may be a plurality of fluid sources, which may all be living sources or non-living sources or a combination of living and non-living sources.

In the illustrated embodiment, the fluid separation chamber 14 is carried within a rotating assembly and, specifically within an annular gap 18 between a rotating spool 20 and bowl 22 of the centrifuge 10. The interior bowl wall 24 defines the high-G wall of a centrifugal field during use of the centrifuge 10, while the exterior spool wall 26 defines the low-G wall of the centrifugal field, as will be described in greater detail herein. Further details of an exemplary centrifuge which is suitable for use with fluid separation chambers according to the present disclosure are set forth in U.S. Pat. No. 5,370,802 to Brown, which is hereby incorporated herein by reference. In one embodiment, the centrifuge 10 comprises a component of a blood processing device of the type currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696 to Giesler et al., which is hereby incorporated herein by reference. Another example of a centrifuge and disposable flow circuit into which aspects of the present disclosure may be incorporated are the ALYX® centrifugal blood processing system sold by Fenwal, Inc. and the disposable flow circuit configured for use therewith, as described in greater detail in U.S. Pat. No. 6,322,488 to Westberg et al., which is hereby incorporated herein by reference. However, as noted above, apparatus and methods described herein are not limited to separation of a particular substance and the illustrated fluid processing device 12 is merely exemplary.

Figure 2:
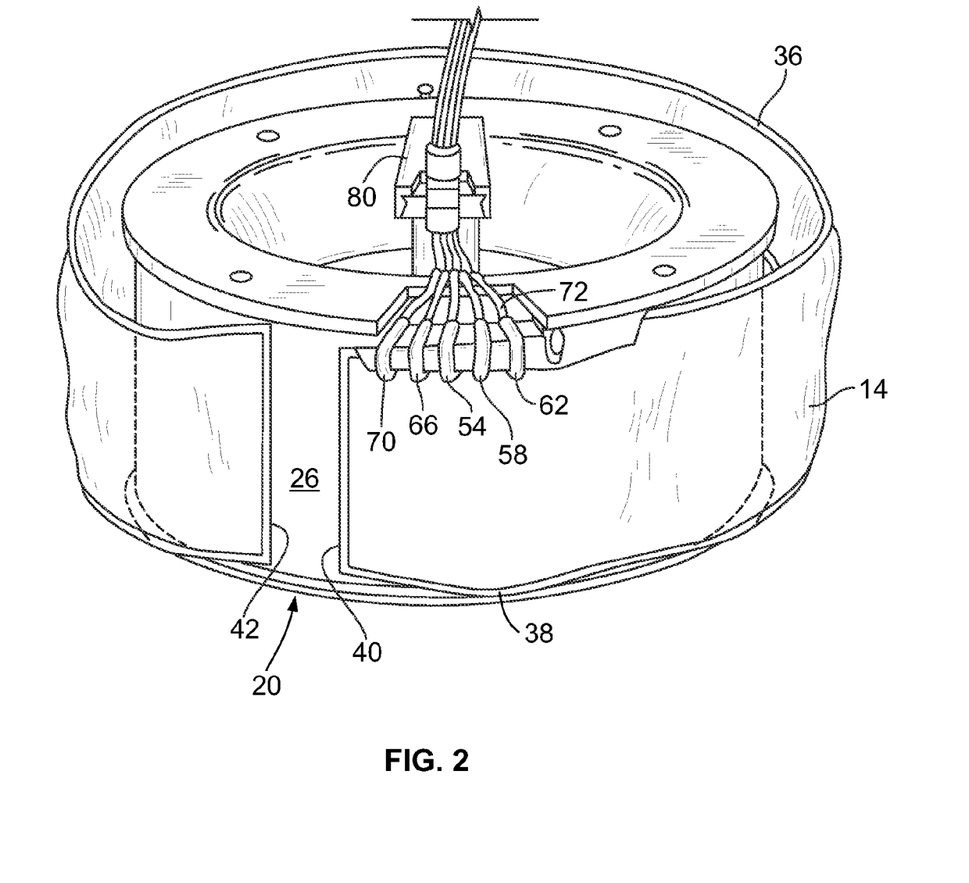
FIG. 2 shows the spool of the centrifuge of FIG. 1, with a fluid separation chamber wrapped about it for use.
Figure 3A:
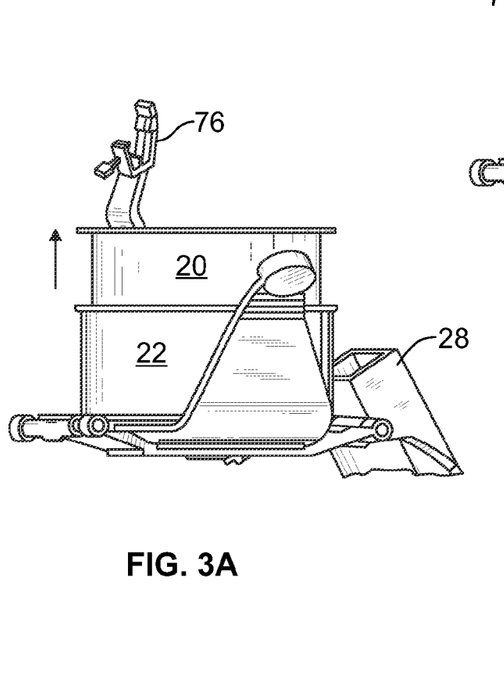
FIG. 3A is a perspective view of the centrifuge shown in FIG. 1, with the bowl and spool thereof pivoted into a loading/unloading position and in a mutually separated condition to allow the fluid separation chamber shown in FIG. 2 to be secured about the spool.
Figure 3B:
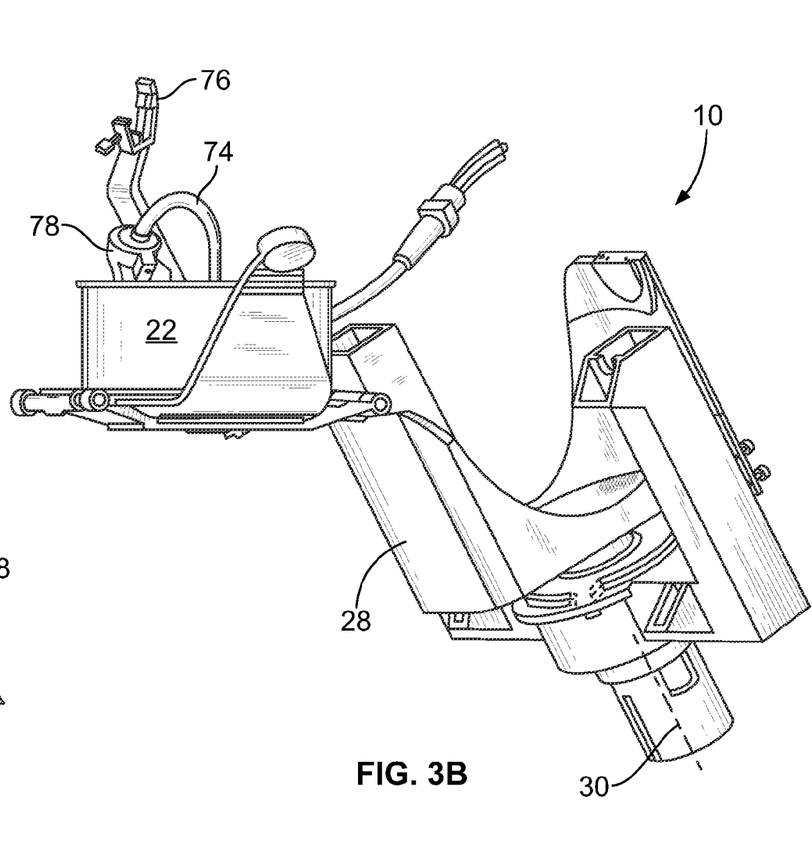
FIG. 3B is a perspective view of the bowl and spool in the loading/unloading position of FIG. 3A, with the bowl and spool in a closed condition after receiving the fluid separation chamber of FIG. 2.

The bowl 22 and spool 20 are pivoted on a yoke 28 between an upright loading/unloading position, as shown in FIGS. 3A and 3B, and an operating position, as FIG. 1 shows. When upright, the bowl 22 and spool 20 are oriented for access by a user or technician. A mechanism permits the spool 20 and bowl 22 to be opened or separated (FIG. 3A) so that the operator can wrap the illustrated flexible fluid separation chamber 14 about the spool 20, as shown in FIG. 2.

When the fluid separation chamber 14 has been properly positioned, the spool 20 may be moved back into the bowl 22 (FIG. 3B), and the spool 20 and bowl 22 can be pivoted into the operating position of FIG. 1. As will be described in greater detail herein, the centrifuge 10 rotates the bowl 22 spool 20 about an axis 30, creating a centrifugal field within the fluid separation chamber 14 to separate or fractionate a fluid.

The illustrated fluid separation chamber 14 is provided with a plurality of stages or sub-chambers, such as a first stage or sub-chamber or compartment and a second stage or sub-chamber or compartment. For purposes of this description, the terms "first" and "second" are denominational only for purposes of identification and do not refer to or require a particular sequence of operation or fluid flow.

Figure 4:
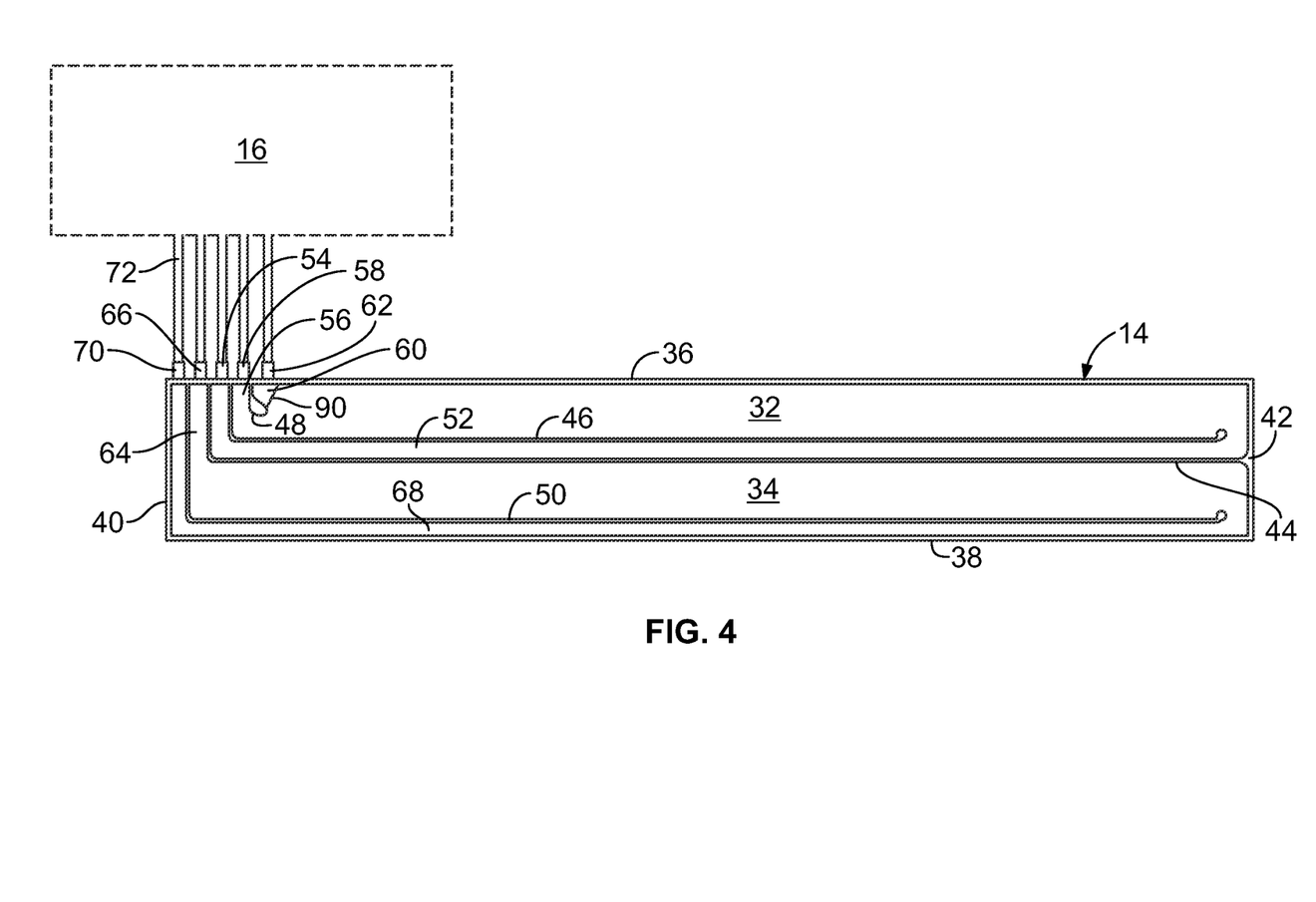
FIG. 4 is a plan view of the fluid separation chamber shown in FIG. 2.

The stages may be variously configured and located within the fluid separation chamber, but in the illustrated embodiment, the first and second stages are positioned at different axial locations (with respect to the axis 30) when the fluid separation chamber 14 is loaded within the centrifuge 10. FIG. 4 illustrates an exemplary fluid separation chamber 14 having such first and second stages 32 and 34. By employing stages which are spaced along the axis 30, the centrifuge 10 does not tend to become imbalanced during use if one of the stages contains a fluid while the other is empty. However, it should be understood that the present disclosure is not limited to fluid separation chambers with stages that are spaced along a rotational axis, but may also include single-stage fluid separation chambers and/or multi-stage fluid separation chambers with stages that are spaced at the same general location along a rotational axis or otherwise configured.

In the embodiment illustrated in FIG. 4, the fluid separation chamber 14 is provided as a flexible body with a seal extending around its perimeter to define a top edge 36, a bottom edge 38, and a pair of side edges 40 and 42. A first interior seal or wall 44 divides the interior of the fluid separation chamber 14 into first and second stages 32 and 34. FIG. 4 shows the first stage 32 positioned above the second stage 34, but the orientation of the stages 32 and 34 is reversed when the fluid separation chamber 14 has been mounted within the centrifuge 10 (FIG. 1). Hence, the first stage 32 may be considered the "lower stage," while the second stage 34 may be considered the "upper stage" when the centrifuge 10 is in an operating position. However, it is within the scope of the present disclosure to provide a first stage which is positioned above the second stage (i.e., at a higher elevation along the rotational axis) during use. Furthermore, it is also within the scope of the present disclosure for the fluid separation chamber to have a single stage or compartment or more than two stages or compartments.

In the illustrated embodiment, the first interior wall 44 extends in a dogleg or L-shaped manner from the top edge 36 toward the bottom edge 38, but extends to terminate at one of the side edges 42 without contacting the bottom edge 38. Thus, the region of the interior of the fluid separation chamber 14 defined by the top edge 36, the first interior wall 44, and the right side edge 42 comprises the first stage 32, while the region defined by the top edge 36, the bottom edge 38, the first interior wall 44, and the two side edges 40 and 42 comprises the second stage 34. It will be seen that, in the embodiment of FIG. 4, the first stage 32 is, in substantial part, spaced from the bottom edge 38 of the fluid separation chamber 14 by the second stage 34.

In addition to the first interior wall 44, the illustrated fluid separation chamber 14 includes additional interior walls or seals. The first stage 32 includes two interior seals or walls 46 and 48, which are referred to herein as second and third interior walls, respectively. The second stage 34 includes one interior seal or wall 50, which is referred to herein as the fourth interior wall. In the embodiment of FIG. 4, each interior wall extends in a dogleg or L-shaped manner from the top edge 36 toward the bottom edge 38 and then (in varying degrees) toward the right side edge 42, without contacting either the bottom edge 38 or the right side edge 42. It is within the scope of the present disclosure for these interior walls to be otherwise configured without departing from the scope of the present disclosure. Further, it is within the scope of the present disclosure for the fluid separation chamber to include more or fewer than four interior walls or seals.

The interior walls of the fluid separation chamber 14 help to define fluid passages which allow for fluid communication between the flow circuit 16 and the first and second stages 32 and 34. In the embodiment of FIG. 4, a first fluid passage 52 is defined at least in part by the first and second interior walls 44 and 46 to allow fluid communication between the first stage 32 and the flow circuit 16 via a port 54 extending through the top edge 36. A second fluid passage 56 is defined at least in part by the second and third interior walls 46 and 48 to allow fluid communication between the first stage 32 and the flow circuit 16 via a port 58 extending through the top edge 36. A third fluid passage 60 is defined at least in part by the third interior wall 48 and the top edge 36 to allow fluid communication between the first stage 32 and the flow circuit 16 via a port 62 extending through the top edge 36. A fourth fluid passage 64 is defined at least in part by the first and fourth interior walls 44 and 50 to allow fluid communication between the second stage 34 and the flow circuit 16 via a port 66 extending through the top edge 36. A fifth fluid passage 68 is defined at least in part by the fourth interior wall 50, the left side edge 40, and the bottom edge 38 to allow fluid communication between the second stage 34 and the flow circuit 16 via a port 70 extending through the top edge 36. While FIG. 4 shows all of the ports and fluid passages associated with the top edge, it is within the scope of the present disclosure for one or more of the ports and fluid passages to be instead associated with a side edge or bottom edge of the fluid separation chamber. An exemplary use for each of the fluid passages during a fluid separation procedure will be described in greater detail below.

The ports may be made of a generally more rigid material and configured to accommodate flexible tubing 72 which connects the fluid separation chamber 14 to the remainder of the flow circuit 16. In the illustrated embodiment, portions of the tubing 72 are joined to define an umbilicus 74 (FIG. 1). A non-rotating (zero omega) holder 76 holds an upper portion of the umbilicus 74 in a non-rotating position above the spool 20 and bowl 22. A holder 78 on the yoke 28 rotates an intermediate portion of the umbilicus 74 at a first (one omega) speed about the spool 20 and bowl 22. Another holder 80 rotates a lower end of the umbilicus 74 at a second speed twice the one omega speed (referred to herein as the two omega speed), at which the spool 20 and bowl 22 also rotate to create a centrifugal field within the fluid separation chamber 14. This known relative rotation of the umbilicus 74 keeps it untwisted, in this way avoiding the need for rotating seals.

Figure 5:
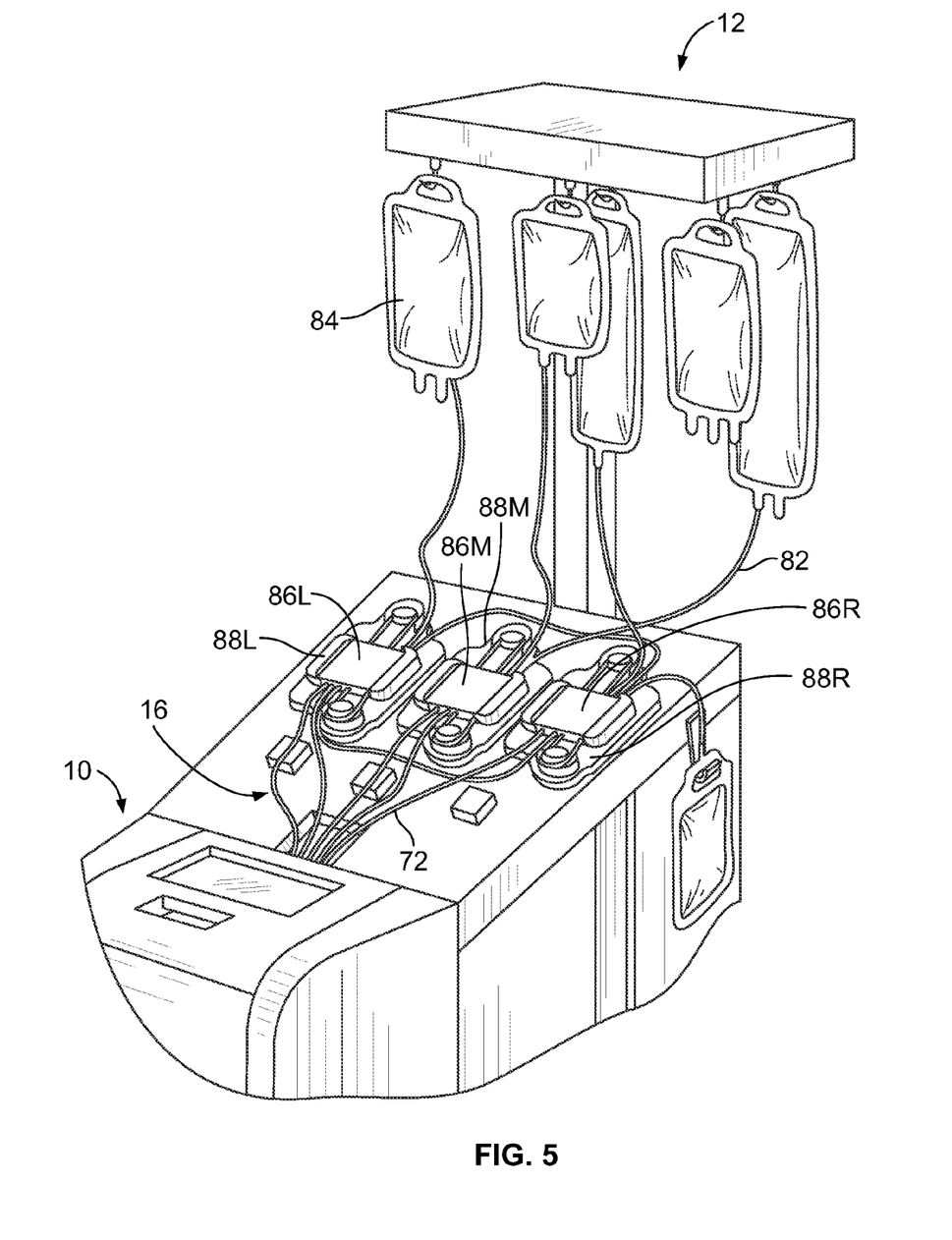
FIG. 5 is a perspective view of a disposable flow circuit (of which the fluid separation chamber comprises a component), which includes cassettes or pump devices mounted in association with pump stations of a fluid separation device (of which the centrifuge comprises a component)

FIG. 5 shows the general layout of an exemplary flow circuit 16, in terms of an array of flexible tubing 82, fluid source and collection containers 84, and fluid-directing cassettes or pump devices. In the illustrated embodiment, left, middle, and right cassettes 86L, 86M, and 86R (respectively), centralize many of the valving and pumping functions of the flow circuit 16. The left, middle, and right cassettes 86L, 86M, and 86R mate with left, middle, and right pump stations 88L, 88M, and 88R (respectively) of the fluid processing device 12. The tubing 82 couples the various elements of the flow circuit 16 to each other and to a fluid source, which may be a human body, but may also be one of the containers 84 or some other non-human source. Additional details of an exemplary flow circuit and fluid processing device suitable for use with fluid separation chambers according to the present disclosure are set forth in U.S. Pat. No. 6,582,349 to Cantu et al., which is hereby incorporated herein by reference.

The fluid separation chamber 14 may be used for either single- or multi-stage processing. When used for single-stage processing, a fluid is continuously flowed into one of the stages (typically the first stage 32), with the fluid separation chamber 14 being rotated by the centrifuge 10 at a speed that is sufficient to separate the fluid into at least two components. All or a portion of one or both of the components may then be flowed out of the first stage 32 and harvested or returned to the fluid source. In a preferred embodiment, the fluid separation chamber 14 is rotated at a "soft spin" speed that is suitable for separating platelet-rich plasma from the other fluid components (e.g., red blood cells, if the fluid is whole blood). The whole blood enters the first stage 32 via port 58 and the second fluid passage 56 (FIG. 4). The centrifugal field present in the fluid separation chamber 14 acts upon the blood to separate it into a layer substantially comprised of platelet-rich plasma and a layer substantially comprised of red blood cells. The higher density component (e.g., red blood cells) gravitates toward the high-G wall 24, while the lower density component (e.g., platelet-rich plasma) remains closer to the low-G wall 26 (FIG. 1). The red blood cells are flowed out of the first stage 32 via port 54 and the first fluid passage 52 (FIG. 4), where they are either harvested or returned to the blood source. The platelet-rich plasma is then flowed out of the first stage 32 for subsequent collection and/or processing, as will be described in greater detail herein. The fluid processing device 12 or a separate device may include an optical sensor associated with the stage in which the platelet-rich plasma is isolated and/or tubing through which the platelet-rich plasma exits such stage to monitor the concentration of the platelet-rich plasma.

When used for multi-stage processing, a fluid is continuously flowed into the first stage 32 as the fluid separation chamber 14 is rotated by the centrifuge. The fluid in the first stage 32 is separated into at least a first component and a second component, based on their differing specific gravities. At least a portion of one of the components is then flowed into the second stage 34, where it is further separated into at least two sub-components. The component not flowed into the second stage 34 may be flowed out of the first stage 32 and harvested or returned to the fluid source. As for the sub-components, at least a portion of one may be flowed out of the second stage 34 for harvesting or return to the fluid source, while the other remains in the second stage 34.

In an exemplary multi-stage fluid processing application, the fluid separation chamber 14 is used to separate whole blood into platelet-rich plasma and red blood cells in the first stage 32. The platelet-rich plasma is then flowed into the second stage 34, where it is separated into platelet concentrate and platelet-poor plasma. In the exemplary procedure, whole blood is flowed into the first stage 32 of a fluid separation chamber 14 received in a spinning centrifuge 10 (as in FIG. 1). The whole blood enters the first stage 32 via port 58 and the second fluid passage 56 (FIG. 4). The centrifugal field present in the fluid separation chamber 14 acts upon the blood to separate it into a layer substantially comprised of platelet-rich plasma and a layer substantially comprised of red blood cells. The higher density component (e.g., red blood cells) gravitates toward the high-G wall 24, while the lower density component (e.g., platelet-rich plasma) remains closer to the low-G wall 26 (FIG. 1). The red blood cells are flowed out of the first stage 32 via port 54 and the first fluid passage 52 (FIG. 4), where they are either harvested or returned to the blood source. The platelet-rich plasma is flowed out of the first stage 32 via port 62 and the third fluid passage 60. The high-G wall 24 may include a projection or dam 90 (FIG. 4) which extends toward the low-G wall 26, across the third fluid passage 60. The dam 90 is configured to intercept red blood cells adjacent thereto and prevent them from entering the third fluid passage 60 and thereby contaminating the platelet-rich plasma. The term "contaminating" as used here means having more of a component (here, more red blood cells) in the fluid flowing to the second stage (here, platelet-rich plasma) than is desired and does not refer to or imply a biological hazard.

The platelet-rich plasma flowed out of the first stage 32 is directed into second stage 34, such as by operation of one or more of the flow control cassettes of the flow circuit 16. The platelet-rich plasma enters the second stage 34 via port 66 and the fourth fluid passage 64. The centrifugal field acts upon the platelet-rich plasma to separate it into a layer substantially comprised of platelet concentrate and a layer substantially comprised of platelet-poor plasma. The higher density component (e.g., platelet concentrate) gravitates toward the high-G wall 24, while the lower density component (e.g., platelet-poor plasma) remains closer to the low-G wall 26 (FIG. 1). The platelet-poor plasma is flowed out of the second stage 34 via port 70 and the fifth fluid passage 68 (FIG. 4), where it is either harvested or returned to the blood source. The platelet concentrate remains in the second stage 34, where it may be stored for later use.

In a preferred embodiment, the platelet-poor plasma removed from the second stage 34 in such a multi-stage separation procedure may be returned to the second stage 34 to combine with the platelet concentrate to create reconstituted platelet-rich plasma. As used herein, the term "platelet-rich plasma" includes platelet-rich plasma as a fluid separated from blood or any other fluid (as in the single-stage separation procedure described above), as well as reconstituted platelet-rich plasma. The concentration of the reconstituted platelet-rich plasma obtained as a product of a multi-stage separation procedure may be varied, depending on the amount of platelet-poor plasma that is returned to the second stage 34. The fluid processing device 12 or a separate device may include an optical sensor associated with the stage in which the platelet-rich plasma is isolated and/or tubing through which the platelet-rich plasma exits such stage to monitor the concentration of the platelet-rich plasma. The ability to adjust the concentration of the platelet-rich plasma may be advantageous if the contemplated use of the platelets is enhanced by a platelet concentration that is greater than what is typically achieved via single-stage separation of platelet-rich plasma.

Figure 6:
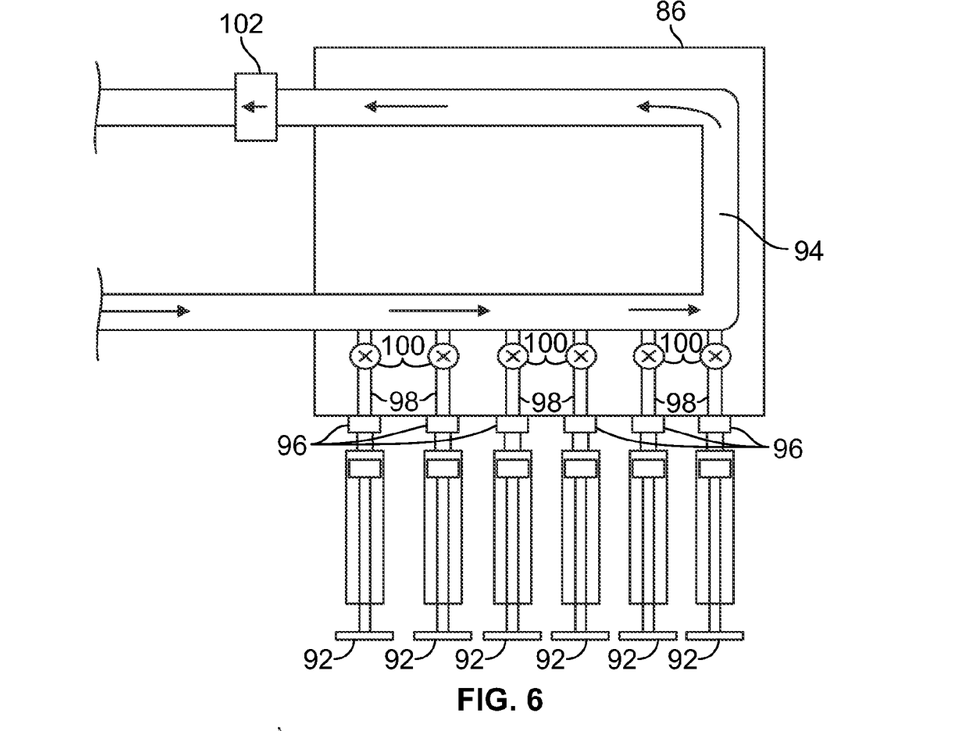
FIG. 6 is a plan view of an alternative cassette or pump device that may be incorporated into disposable flow circuits, such as the one illustrated in FIG. 5.

When the platelet-rich plasma has been isolated within the fluid separation chamber 14 (either by being separated from blood or any other platelet-containing fluid or by platelet concentrate being separated and then reconstituted using platelet-poor plasma), all or a portion of the platelet-rich plasma may be automatically transferred from the fluid separation chamber 14 to an injection device, such as a syringe (with or without a pre-attached needle). Preferably, the injection device is incorporated into the disposable flow circuit 16, as part of a closed system that is pre-sealed and sterilized. In one exemplary embodiment, which is illustrated in FIG. 6, one of the cassettes or pump devices 86 of the disposable flow circuit 16 has one or more injection devices 92 connected thereto. In the illustrated embodiment, there are six injection devices 92 connected to one of the sides of the cassette 86, but any number of injection devices may be connected to the cassette 86 at any suitable location. In contrast to known batch-type systems, continuous flow-type systems, such as the one described herein, typically allow for a greater amount of fluid to be processed and, hence, a greater amount of platelet-rich plasma to be collected. Thus, by employing a continuous flow-type system, a plurality of therapeutic injections may be prepared during a single fluid draw, without requiring the system to be reloaded with additional fluid containers for separation or requiring a single, filled injection device to be replaced with an empty injection device for receipt of additional platelet-rich plasma.

In the embodiment of FIG. 6, each injection device 92 is connected to the fluid flow path 94 defined through the cassette 86. In one embodiment, the fluid flow path 94 through the cassette 86 is defined by rigid walls and at least one flexible membrane or sheet of material that is alternately flexed to move fluid through the flow path 94, but the fluid flow path may be otherwise defined without departing from the scope of the present disclosure. In the illustrated embodiment, the cassette 86 includes an access port or opening 96 for each associated injection device 92. Preferably, the injection devices 92 are pre-connected to the cassette 86 to ensure that the disposable flow circuit 16 comprises a closed system, but it is also within the scope of the present disclosure for the injection devices 92 to be separately provided and connectable to the cassette 86 via the ports 96. If the injection devices 92 are separately provided, the ports 96 may include frangible sterile seals or the like that isolate the interior of the cassette 86 from the outside environment prior to the injection devices 92 being inserted into the ports 96.

Each port 96 is fluidly connected to the flow path 94, such as by a valved channel 98 or the like. If provided as shown in FIG. 6, the aforementioned flexible membrane used to enable flow through the flow path 94 may cooperate with a valve 100 in each channel 98 to control flow through the associated channel 98. For example, each valve 100 may include an opening or passage that is typically covered by the flexible membrane to prevent fluid flow through the channel 98. When it is desirable to allow fluid flow into one or more of the injection devices 92, a force may be applied to the flexible membrane in the vicinity of the valve 100 to unseat the membrane from the valve 100, thereby opening the valve 100 and allowing fluid (e.g., platelet-rich plasma) to flow from the flow path 94 into the appropriate injection device 92. Other valving arrangements may also be employed without departing from the scope of the present disclosure. For example, the valving system may be automatic or manual (e.g., using automated or hand-operated rotary stopcocks or the like) and/or may operate to simultaneously or sequentially transfer platelet-rich plasma into the injection devices. 92. The injection devices 92 may be filled to the same extent as each other or may be filled with different amount of platelet-rich plasma. Furthermore, the injection devices 92 may be differently configured, rather than being substantially identically configured, as shown in FIG. 6.

It should be understood that FIG. 6 shows a simplified version of the configuration of a typical cassette or pump device 86, and the cassette 86 may include any of a number of other additional components and be differently configured (e.g., including additional flow paths and ports) without departing from the scope of the present disclosure. By way of example, the cassette 86 may include a one-way valve 102 to prevent contamination of the isolated platelet-rich plasma by other fluids (e.g., whole blood or packed red cells) during use. Furthermore, if a plurality of cassettes or pump devices are provided, as illustrated in FIG. 5, each may be provided with one or more associated injection device 92, rather than all of the injection devices 92 being associated with a single cassette or pump device.

Figure 7:
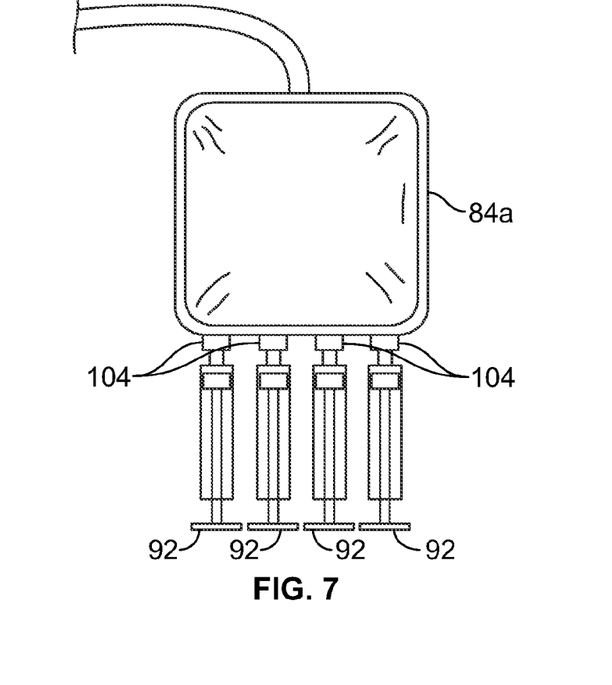
FIG. 7 is a plan view of an alternative collection container that may be incorporated into disposable flow circuits, such as the one illustrated in FIG. 5.

In another exemplary embodiment, which is illustrated in FIG. 7, one or more of the fluid collection containers 84a of the disposable flow circuit 16 has one or more injection devices 92 connected thereto. In the illustrated embodiment, there are four injection devices 92 connected to a bottom side or edge of the container 84a, but any number of injection devices may be connected to the container 84a at any suitable location. While FIG. 7 illustrates a single collection container 84a having one or more injection devices 92 associated therewith, it is also within the scope of the present disclosure for a plurality of the containers of the fluid circuit 16 to include one or more associated injection devices 92. It is also within the scope of the present disclosure for the injection devices 92 to be connected at different locations of the fluid circuit 16 (e.g., both at the pump device 86 and the collection container 84a), including locations not specifically illustrated and/or described herein. Furthermore, the various injection devices may be differently configured and/or sized, rather than being substantially identical as shown in FIG. 7.

In the embodiment of FIG. 7, each injection device 92 is connected to the container 84a by an access port or opening 104, which may be similar to the access ports 96 of FIG. 6. Preferably, the injection devices 92 are pre-connected to the container 84a to ensure that the disposable flow circuit 16 comprises a closed system, but it is also within the scope of the present disclosure for the injection devices 92 to be separately provided and connectable to the container 84a via the ports 104. If the injection devices 92 are separately provided, the ports 104 may include frangible sterile seals or the like that isolate the interior of the container 84a from the outside environment prior to the injection devices 92 being inserted into the ports 104.

Each port 104 is fluidly connected to the container 84a by any suitable means, such as by a valved or open channel. Alternatively, the ports 104 may open directly into the interior of the container 84a and may have built-in valves to selectively open and close fluid communication between the container 84a and the associated injection device 92. If valves are provided, they may be variously configured without departing from the scope of the present disclosure. For example, the valves may be configured for manual or automatic actuation. If the valves are to be automated, they may be controlled by a valve actuator of the fluid processing device 12 or a separate controller device, with the configuration of the particular valve actuator depending upon the configuration of the corresponding valve. The injection devices 92 may be filled sequentially or simultaneously and may be filled to the same extent as each other or with different amount of platelet-rich plasma.

When the injection devices 92 have been sufficiently filled with platelet-rich plasma, they may be detached from the remainder of the disposable flow circuit 16 for subsequent use in a therapeutic injection procedure. If desired, a growth factor solution or any other additive may be added to the platelet-rich plasma prior to therapeutic injection. If an additive is to be mixed with the platelet-rich plasma, the additive may be maintained in the container 84a to which the injection devices 92 are connected, if one or more of the collection containers is configured as in FIG. 7. Alternatively, the additive may be provided in a separate container and added to the platelet-rich plasma either while it is isolated in the fluid separation chamber 14 or after it has been transferred out of the fluid separation chamber 14. The additive may also be initially present in one or more of the injection devices 92.

EXAMPLES

Without limiting any of the foregoing, the subject matter described herein may be found in one or more apparatus or methods. For example, according to a first exemplary method of processing a fluid containing blood plasma and platelets, such fluid is continuously added into a fluid separation chamber. Platelet-rich plasma is isolated in the fluid separation chamber and at least a portion of the platelet-rich plasma is automatically transferred from the fluid separation chamber into an injection device.

A second exemplary method of the present subject matter includes a method in accordance with the preceding exemplary method, in which the platelet-rich plasma is separated from the fluid.

A third exemplary method of the present subject matter includes a method in accordance with the first exemplary method, in which platelet concentrate and platelet-poor plasma are separated from the fluid, and at least a portion of the platelet-poor plasma is added to the platelet concentrate to form platelet-rich plasma.

A fourth exemplary method of the present subject matter includes a method in accordance with the first exemplary method, in which the fluid comprises blood, and the blood is drawn from a blood source into the fluid separation chamber prior to isolating platelet-rich plasma by separating packed red blood cells from the blood. At least a portion of the packed red blood cells is automatically transferred from the fluid separation chamber to the blood source.

A fifth exemplary method of the present subject matter includes a method in accordance with any one of exemplary methods 1-4, in which the platelet-rich plasma is automatically transferred from the fluid separation chamber into a collection container connected to the injection device prior to transferring the platelet-rich plasma into the injection device.

A sixth exemplary method of the present subject matter includes a method in accordance with any one of exemplary methods 1-5, in which the platelet-rich plasma is automatically transferred from the fluid separation chamber into a pump device connected to the injection device prior to transferring the platelet-rich plasma into the injection device.

A seventh exemplary method of the present subject matter includes a method in accordance with any one of exemplary methods 1-6, in which the fluid separation chamber and the injection device comprise components of a closed system.

An eight exemplary method of the present subject matter includes a method in accordance with the preceding exemplary method, in which the injection device is separated from the closed system after platelet-rich plasma is transferred into the injection device.

A ninth exemplary method of the present subject matter includes a method in accordance with any one of exemplary methods 1-8, in which the platelet-rich plasma is combined with a growth factor solution.

A tenth exemplary method of the present subject matter includes a method in accordance with any of exemplary methods 1-9, in which the platelet-rich plasma is automatically transferred from the fluid separation chamber into a plurality of injection devices.

An eleventh exemplary method of the present subject matter includes a method in accordance with the preceding exemplary method, in which the platelet-rich plasma is sequentially transferred to the plurality of injection devices.

A twelfth exemplary method of the present subject matter includes a method in accordance with the exemplary method 10, in which the platelet-rich plasma is simultaneously transferred to two or more of the injection devices.

In another aspect of this subject matter, a first exemplary disposable flow circuit is provided for use in combination with a fluid processing device for isolating platelet-rich plasma from a fluid containing blood plasma and platelets. The circuit includes a fluid separation chamber, at least one pump device fluidly connected to the fluid separation chamber, and at least one collection container fluidly connected to the fluid separation chamber. At least one injection device is connected to the collection container.

A second exemplary configuration of a disposable flow circuit includes a configuration in accordance with the preceding exemplary configuration, in which the fluid separation chamber, the pump device, the collection container, and the injection device comprise a closed system.

A third exemplary configuration of a disposable flow circuit includes a configuration in accordance with the first or second exemplary configuration, in which the injection device comprises a syringe.

A fourth exemplary configuration of a disposable flow circuit includes a configuration in accordance with any one of exemplary configurations 1-3, in which a plurality of injection devices are connected to the collection container.

A fifth exemplary configuration of a disposable flow circuit for use in combination with a fluid processing device for isolating platelet-rich plasma from a fluid containing blood plasma and platelets includes a fluid separation chamber and at least one pump device fluidly connected to the fluid separation chamber. At least one injection device is connected to the pump device.

A sixth exemplary configuration of a disposable flow circuit includes a configuration in accordance with the preceding exemplary configuration, in which the fluid separation chamber, the pump device, and the injection device comprise a closed system.

A seventh exemplary configuration of a disposable flow circuit includes a configuration in accordance with the fifth or sixth exemplary configuration, in which the injection device comprises a syringe.

An eighth exemplary configuration of a disposable flow circuit includes a configuration in accordance with any one of exemplary configurations 5-7, in which a plurality of injection devices are connected to the pump device.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method for collecting platelet-rich plasma, comprising:
    Mounting a disposable flow circuit to a fluid processing device, the disposable flow circuit including a fluid separation chamber and an injection device;
    Continuously conveying a fluid containing plasma and platelets from a fluid source into the fluid separation chamber;
    Processing said fluid to produce platelet-rich plasma from the fluid separation chamber;
    Automatically conveying at least a portion of the platelet-rich plasma from the fluid separation chamber into the injection device, wherein the injection device is directly connected to a pump device and at least a portion of the platelet-rich plasma from the fluid separation chamber is automatically conveyed into the pump device prior to conveying said at least a portion of the platelet-rich plasma into the injection device; and
    Detaching the injection device with said at least a portion of the platelet-rich plasma from the disposable flow circuit.

2. The method of claim 1, wherein said processing said fluid to produce platelet-rich plasma in the fluid separation chamber includes separating platelet-rich plasma from at least one other component of said fluid in the fluid separation chamber.

3. The method of claim 1, wherein said processing said fluid to produce platelet-rich plasma in the fluid separation chamber includes
separating platelet concentrate from platelet-poor plasma in the fluid separation chamber, and
adding at least a portion of the platelet-poor plasma to the platelet concentrate in the fluid separation chamber to produce reconstituted platelet-rich plasma.

4. The method of claim 1, wherein
the fluid comprises blood,
said continuously conveying the fluid containing plasma and platelets into the fluid separation chamber includes drawing blood from the fluid source into the fluid separation chamber prior to producing platelet-rich plasma in the fluid separation chamber,
said processing said fluid to produce platelet-rich plasma in the fluid separation chamber includes separating packed red blood cells from the blood, and further comprising
automatically conveying at least a portion of the packed red blood cells from the fluid separation chamber to the fluid source.

5. The method of claim 1, wherein said automatically conveying at least a portion of the platelet-rich plasma from the fluid separation chamber into the injection device includes automatically conveying said at least a portion of the platelet-rich plasma from the fluid separation chamber into a collection container directly connected to the injection device prior to conveying said at least a portion of the platelet-rich plasma into the injection device.

6. The method of claim 1, wherein the disposable flow circuit is a closed system.

7. The method of claim 1, further comprising combining said at least a portion of the platelet-rich plasma with a growth factor solution.

8. The method of claim 1, wherein said automatically conveying at least a portion of the platelet-rich plasma from the fluid separation chamber into the injection device includes automatically conveying said at least a portion of the platelet-rich plasma from the fluid separation chamber into the injection device while processing said fluid to produce platelet-rich plasma in the fluid separation chamber.

9. A method for collecting platelet-rich plasma, comprising:
mounting a disposable flow circuit to a fluid processing device, the disposable flow circuit including a fluid separation chamber, a pump device fluidly connected to the fluid separation chamber, and an injection device directly connected to the pump device;
operating the fluid processing device to process a fluid containing plasma and platelets so as to produce platelet-rich plasma in the fluid separation chamber while the injection device is directly connected to the pump device;
operating the pump device to convey the platelet-rich plasma out of the fluid separation chamber; and
conveying at least a portion of the platelet-rich plasma into the injection device directly connected to the pump device.

10. The method of claim 9, wherein the disposable flow circuit is a closed system.

11. The method of claim 9, wherein
the pump device comprises a cassette defining a fluid flow path, and
the injection device is directly connected to the fluid flow path.

12. The method of claim 9, wherein the pump device defines a fluid flow path and includes an access port receiving a portion of the injection device and a valved channel connecting the access port to the fluid flow path, and further comprising actuating a valve of the valved channel to selectively allow and prevent fluid flow from the fluid flow path into the injection device.

13. The method of claim 12, wherein
the pump device includes a flexible membrane, and
said actuating the valve of the valved channel to selectively allow and prevent fluid flow from the fluid flow path into the injection device includes alternately flexing the flexible membrane to selectively allow and prevent fluid flow from the fluid flow path into the injection device.

14. The method of claim 9, further comprising detaching the injection device with said at least a portion of the platelet-rich plasma from the pump device after said conveying said at least a portion of the platelet-rich plasma into the injection device directly connected to the pump device, wherein the injection device remains directly connected to the pump device between said mounting the disposable flow circuit to the fluid processing device and said detaching the injection device with said at least a portion of the platelet-rich plasma from the pump device.

* * * * *